(12) United States Patent
Herring et al.

(10) Patent No.: US 10,828,201 B2
(45) Date of Patent: Nov. 10, 2020

(54) HEARING PROTECTION DEVICE

(71) Applicants: Kirk Herring, Fort Worth, TX (US); Matthew Weinrich, Richland Hills, TX (US)

(72) Inventors: Kirk Herring, Fort Worth, TX (US); Matthew Weinrich, Richland Hills, TX (US)

(*) Notice: Subject to any disclaimer, the term of this patent is extended or adjusted under 35 U.S.C. 154(b) by 387 days.

(21) Appl. No.: 15/911,621

(22) Filed: Mar. 5, 2018

(65) Prior Publication Data

US 2018/0250168 A1  Sep. 6, 2018

Related U.S. Application Data

(60) Provisional application No. 62/466,802, filed on Mar. 3, 2017.

(51) Int. Cl.
| | |
|---|---|
| *H04R 1/10* | (2006.01) |
| *A61F 11/12* | (2006.01) |
| *A45F 5/02* | (2006.01) |
| *A45F 5/00* | (2006.01) |
| *H04R 5/033* | (2006.01) |
| *A42B 1/24* | (2006.01) |
| *A61F 11/08* | (2006.01) |

(52) U.S. Cl.
CPC .............. *A61F 11/12* (2013.01); *A45F 5/00* (2013.01); *A45F 5/02* (2013.01); *H04R 1/1016* (2013.01); *H04R 1/1033* (2013.01); *H04R 5/033* (2013.01); *A42B 1/24* (2013.01); *A44D 2203/00* (2013.01); *A45F 2200/0508* (2013.01); *A61F 11/08* (2013.01); *H04R 2201/023* (2013.01)

(58) Field of Classification Search
CPC .. H04R 1/1008; H04R 1/1016; H04R 1/1033; H04R 5/033; H04R 2201/023; H04R 2499/11; H04M 1/05; A61F 11/08
USPC ............... 381/309, 370, 374, 376, 380, 384; 378/430, 438
See application file for complete search history.

(56) References Cited

U.S. PATENT DOCUMENTS

| | | | |
|---|---|---|---|
| 4,942,617 A * | 7/1990 | Boylan | H04M 1/05 381/182 |
| 5,193,226 A | 3/1993 | Mortenson | |
| 5,339,461 A * | 8/1994 | Luplow | H04B 1/086 242/385 |
| 5,422,957 A * | 6/1995 | Cummins | B65H 75/4431 381/384 |
| 5,581,821 A | 12/1996 | Nakano | |
| 6,834,820 B2 * | 12/2004 | Wei | B65H 75/4449 191/12.2 R |
| 6,902,029 B2 | 6/2005 | Weise | |

(Continued)

*Primary Examiner* — Huyen D Le
(74) *Attorney, Agent, or Firm* — Brennan, Manna & Diamond, LLC (57) ABSTRACT

A hearing protection device for attaching to a wearable article. The device comprises a housing, a recoil assembly, a cord, and a pair of ear engaging components. The device further comprises a mounting component for attaching the device to the wearable article such as a baseball cap or a helmet. A user may extend the pair of ear engaging components out of or away from the housing for use, and retract the pair of ear engaging components back toward or into the housing when no longer needed. When not in use, the device remains attached to the wearable article so that it is convenient to access when needed.

10 Claims, 8 Drawing Sheets

(56) References Cited

U.S. PATENT DOCUMENTS

| | | | |
|---|---|---|---|
| 6,978,034 B2* | 12/2005 | Lazzeroni | A42B 3/30 |
| | | | 379/430 |
| 7,974,432 B1* | 7/2011 | Ryan | A42B 1/245 |
| | | | 2/195.1 |
| 8,650,666 B2 | 2/2014 | Crutcher | |
| 8,794,758 B2 | 8/2014 | Brauner | |
| 8,798,305 B2* | 8/2014 | Harper | H04R 1/1016 |
| | | | 381/374 |
| 9,167,330 B1 | 10/2015 | Shattuck | |
| 9,486,030 B2 | 11/2016 | Krissman | |
| 2006/0251283 A1 | 11/2006 | Yeh | |
| 2009/0016559 A1* | 1/2009 | Cleary | H04R 1/1091 |
| | | | 381/375 |
| 2009/0199326 A1 | 8/2009 | Brauner | |
| 2015/0129702 A1 | 5/2015 | Brennan et al. | |
| 2015/0373442 A1 | 12/2015 | Saucedo | |
| 2016/0050774 A1 | 2/2016 | Merenda | |
| 2016/0286943 A1 | 10/2016 | Andersen et al. | |
| 2016/0332842 A1 | 11/2016 | Hanson | |

* cited by examiner

HEARING PROTECTION DEVICE

CROSS-REFERENCE

This application claims priority from Provisional Patent Application Ser. No. 62/466,802 filed Mar. 3, 2017.

FIELD OF THE INVENTION

This invention pertains generally to a device for use as universal hearing protection, and more particularly to a device that is conveniently accessible to protect or augment a user's hearing during exposure to excessive noise, yet remains readily accessible to the user when not needed.

BACKGROUND

Exposure to extreme noise or even moderate noise for an extended period of time can damage hearing. Hearing loss is one of the most common work related injuries. Hearing protection devices are often used to reduce noise exposure levels and the associated risk of damage to ear anatomy. However, the effectiveness of existing hearing protectors is greatly reduced if they are only worn intermittently, or not at all. Typical hearing protectors include ear plugs, semi-insert ear plugs, and ear muff styled devices. Ear plugs may be disposable or reusable and are inserted into the ear to block the ear canal from sound transmissions. Semi-insert plugs are held over the ends of the ear canal with a rigid head band. Ear muffs are made of sound attenuating materials and cushions that fit around the ears and are held in place by a head band.

Since it may be uncomfortable or even dangerous to use hearing protection when unnecessary, users commonly remove ear plugs and either throw them away, or store them when not in use. Similarly, semi-insert plugs and earmuffs are commonly removed when unnecessary and set down or stored. It is inconvenient to hold existing forms of hearing protection when not in use, and uncomfortable to simply keep the devices in place when not needed. Additionally, the user would not be able to hear when hearing protection is no longer needed and the protective devices are not removed creating a potential safety hazard. Hearing loss is a common injury for construction workers, safety forces, military forces, mechanics, sport shooters, hunters, anyone listening to music, or anyone that has the potential to experience noise pollution. Despite a wide variety of hearing protection devices commonly available, the devices are useless if not worn each and every time there is a potential exposure to damaging noise.

Consequently, as hearing is no longer protected if the protectors are not worn during episodes of excessive noise, there exists a need for a device that can adequately protect hearing that remains readily available and easily accessible to the user when not needed. The present invention effectively reduces noise pollution and protects hearing when in use, but does not require the user to store or put down the protection while continuing with other tasks when there is no longer a risk of hearing damage. Alternatively, the device may be used to conduct desirable transmissions at safe decibel levels while blocking out ambient or other undesirable noise or sounds.

SUMMARY

The following presents a simplified summary in order to provide a basic understanding of some aspects of the disclosed invention. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises a universal device for protecting a user from the harmful effects of dangerous noise levels while remaining conveniently assessable when not in use. The device comprises a recoil assembly enclosed within a housing, a cord retractably engaging the recoil assembly, and a pair of ear engaging elements. The device further comprises a mounting component attached to the housing for detachably attaching the device to a wearable article.

Furthermore, in a preferred embodiment of the invention the pair of ear engaging elements are attachable to a pair of ends of the cord, and are replaceable once worn, dirty, or otherwise contaminated. The mounting component comprises a strap and a securing element. The strap is used to engage a loop, a hole, or other existing attachment point on the wearable article. The securing element may comprise a pair of magnets to detachably secure the strap to the wearable article for as long as desired without affecting the integrity of the wearable article.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

DETAILED DESCRIPTION

Reference is now made to the drawings, wherein like reference numerals are used to refer to like elements throughout. In the following description, for purposes of explanation, numerous specific details are set forth in order to provide a thorough understanding thereof. It may be evident, however, that the novel embodiments can be practiced without these specific details. In other instances, well known structures and devices are shown in block diagram form in order to facilitate a description thereof. The intention is to cover all modifications, equivalents, and alternatives falling within the spirit and scope of the claimed subject matter. The invention relates generally to a device for protecting a user's hearing that is securable to a wearable article.

Figure 8:
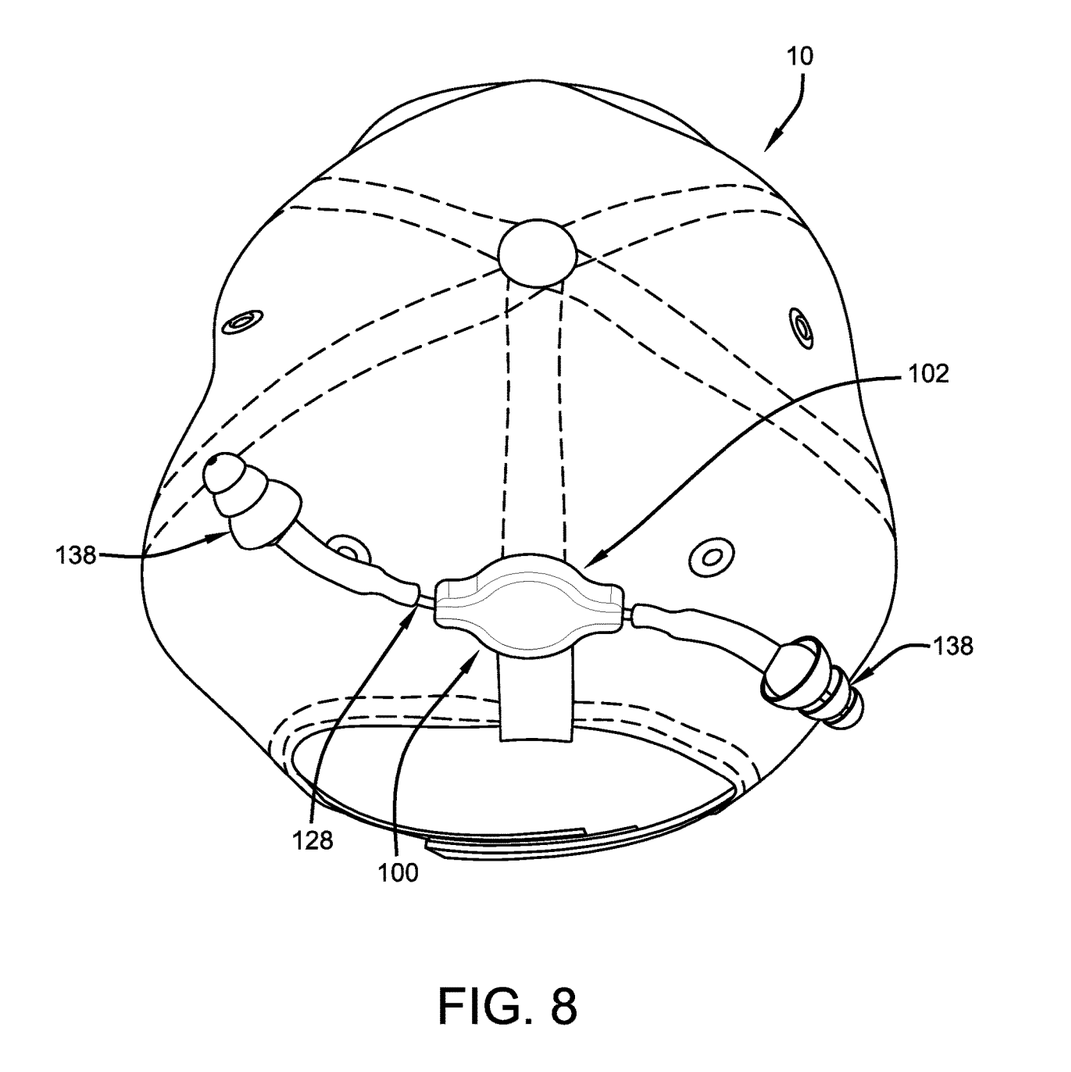
FIG. 8 illustrates a perspective view of the device attached to a wearable article in accordance with the disclosed architecture.

As illustrated in FIGS. 1-8, a device 100 use as hearing protection is disclosed. The device 100 is attachable and securable to a wearable article 10, such as, but not limited to, a hardhat, a helmet, a baseball cap, a head covering, a jacket collar, hunting gear, a cowboy hat, a shirt, hunting gear, and the like. The device 100 is securable to the wearable article 10 without the need for adhesives, a permanent means of attachment, or any kind of modification to the wearable article 10. Once secured to the wearable article 10 as illustrated in FIG. 8, the device 100 is readily accessible for use as hearing protection. When not in use, the device 100 is retracted and simply hangs in place on the wearable article 10 out of the way while remaining conveniently located and easily accessible for future use. The device 100 quickly non-permanently attaches and detaches from any head gear or garment. The device 100 is particularly useful for hunters during the spot and stalk process.

As illustrated in FIGS. 1-4, the device 100 is useable with earplugs, ear buds, headphones, and the like. The device 100 comprises a housing 102, a recoil assembly 120, and a cord 128. The housing 102 comprises a top 104, a bottom 110, and at least one sidewall 112 comprising a pair of openings 114. The housing 102 further comprises an interior 116 for enclosing the recoil assembly 120 as described infra.

Figure 1:
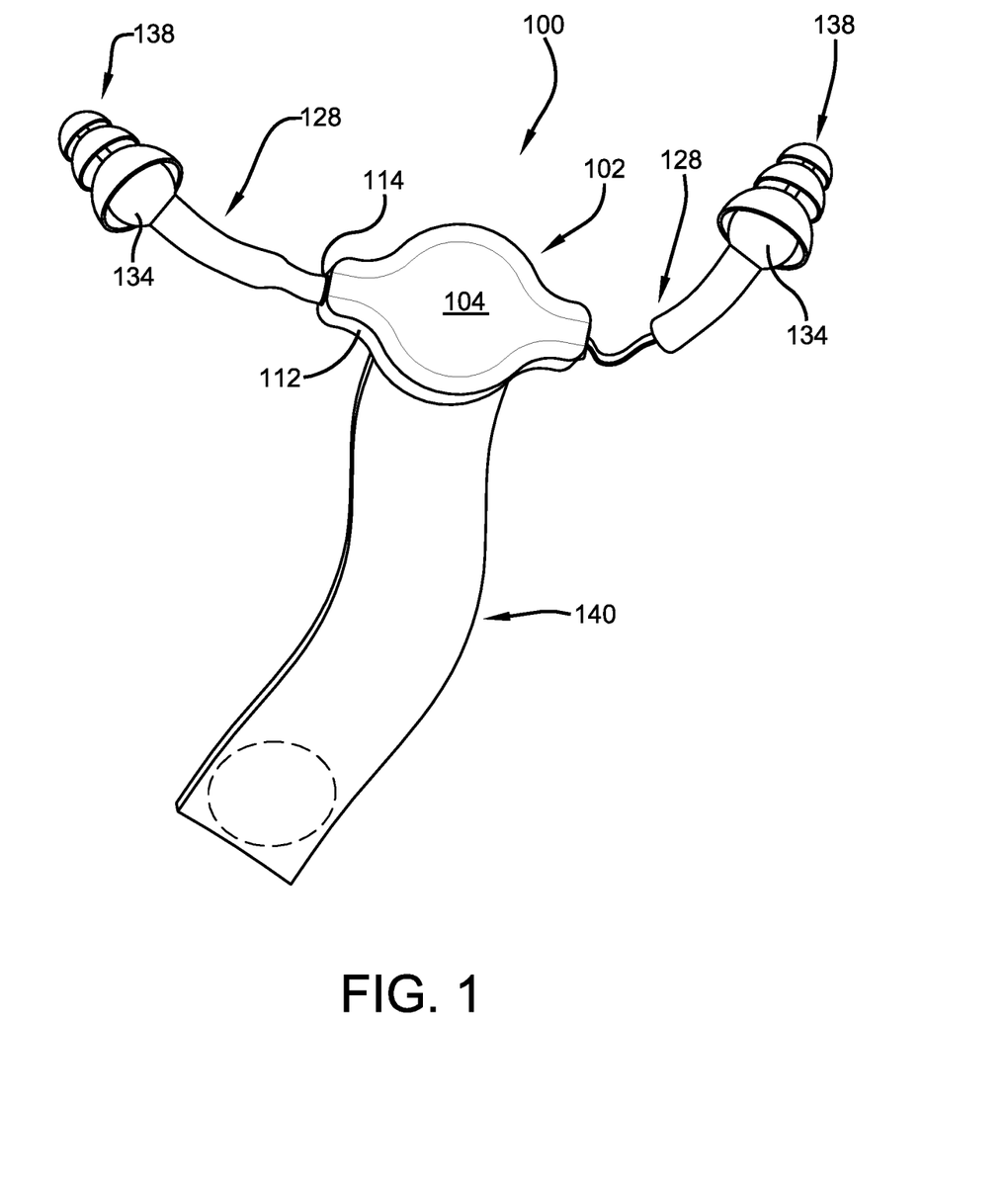
FIG. 1 illustrates a front perspective view of a hearing protection device in accordance with the disclosed architecture.
Figure 2:
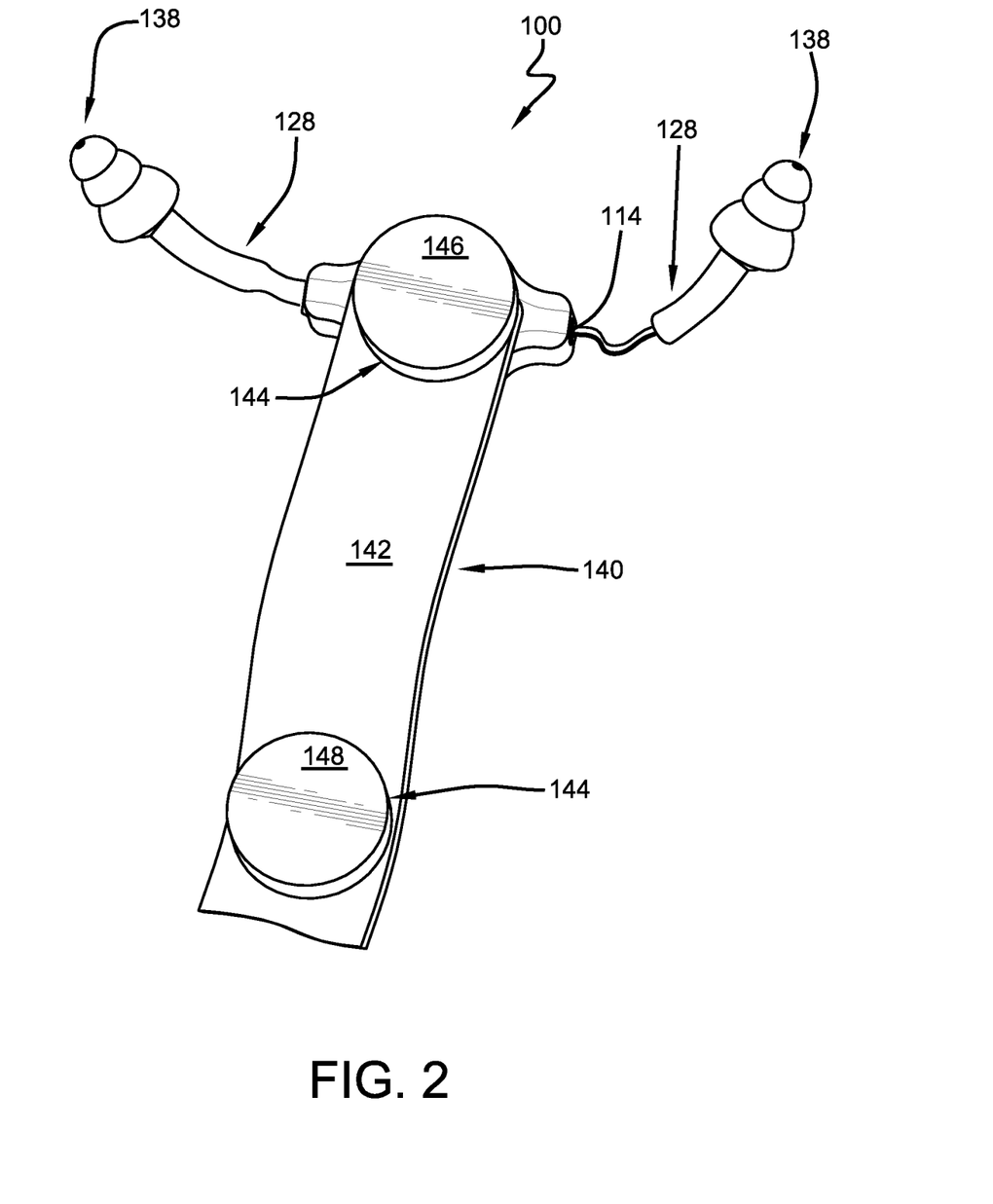
FIG. 2 illustrates a rear perspective view of the device in accordance with the disclosed architecture.
Figure 3:
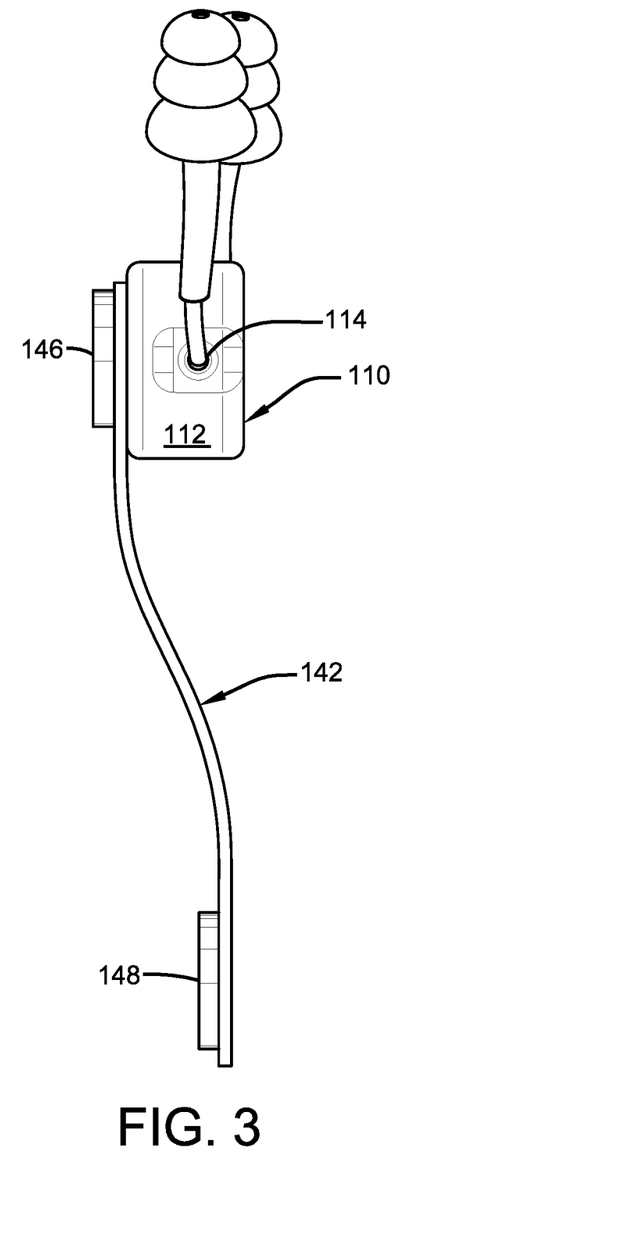
FIG. 3 illustrates a side view of the device in accordance with the disclosed architecture.
Figure 4:
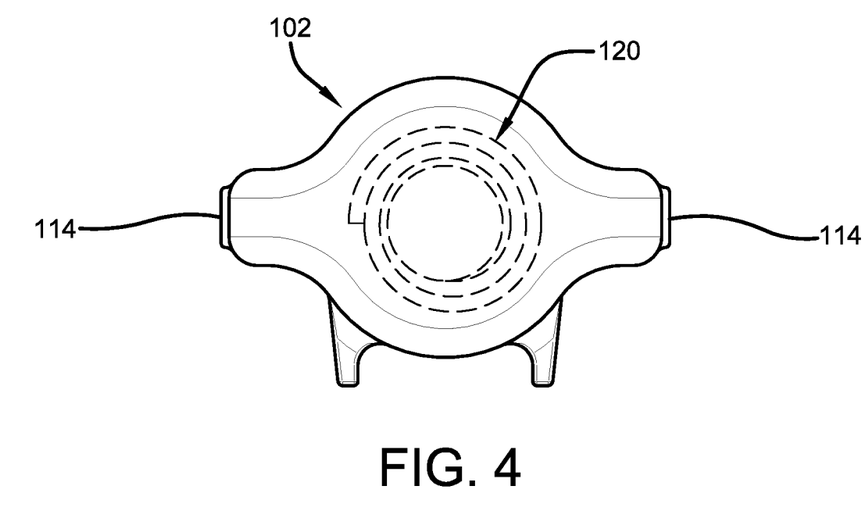
FIG. 4 illustrates a top view of a recoil assembly of the device in accordance with the disclosed architecture.
Figure 4A:
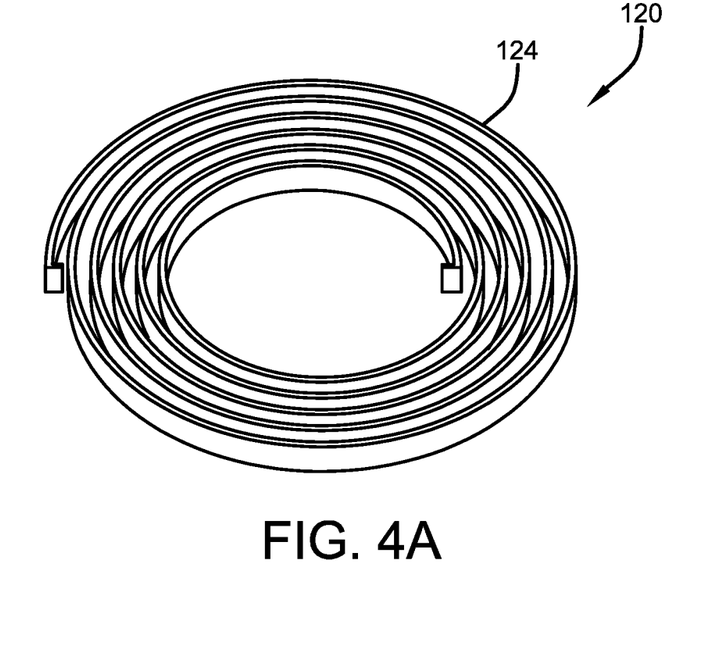
FIG. 4A illustrates a perspective view of the recoil assembly in accordance with the disclosed architecture.
Figure 5:
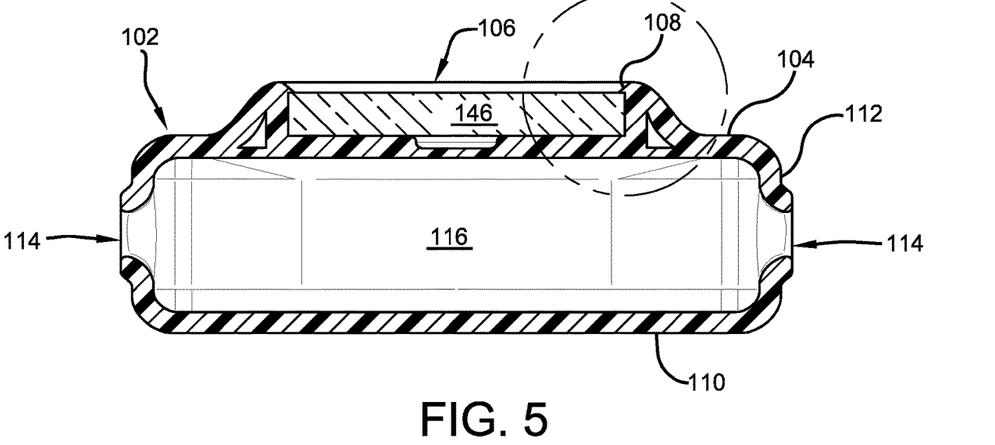
FIG. 5 illustrates a perspective view of a housing of the device in accordance with the disclosed architecture.
Figure 5A:
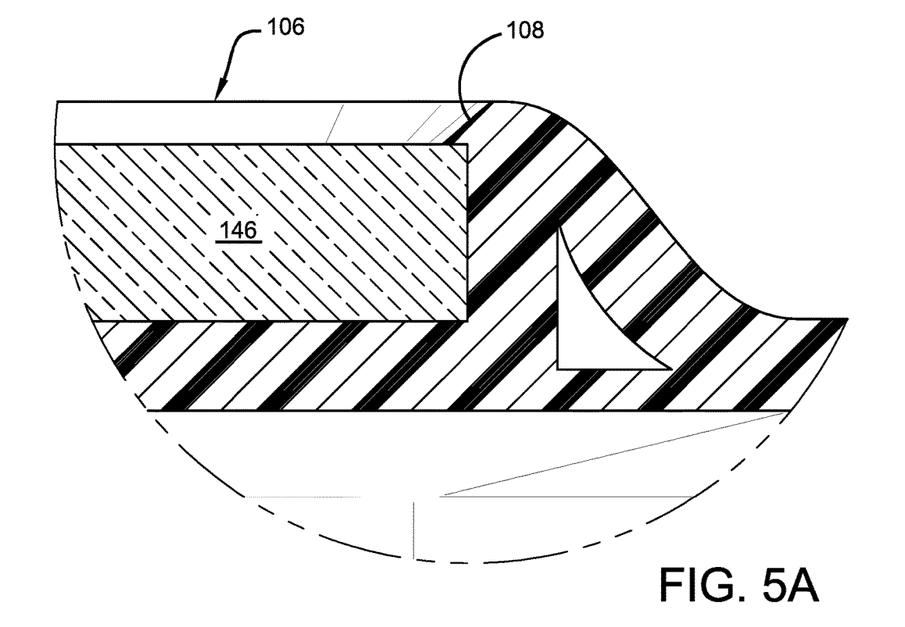
FIG. 5A illustrates a cutaway view of the housing in accordance with the disclosed architecture.
Figure 6:
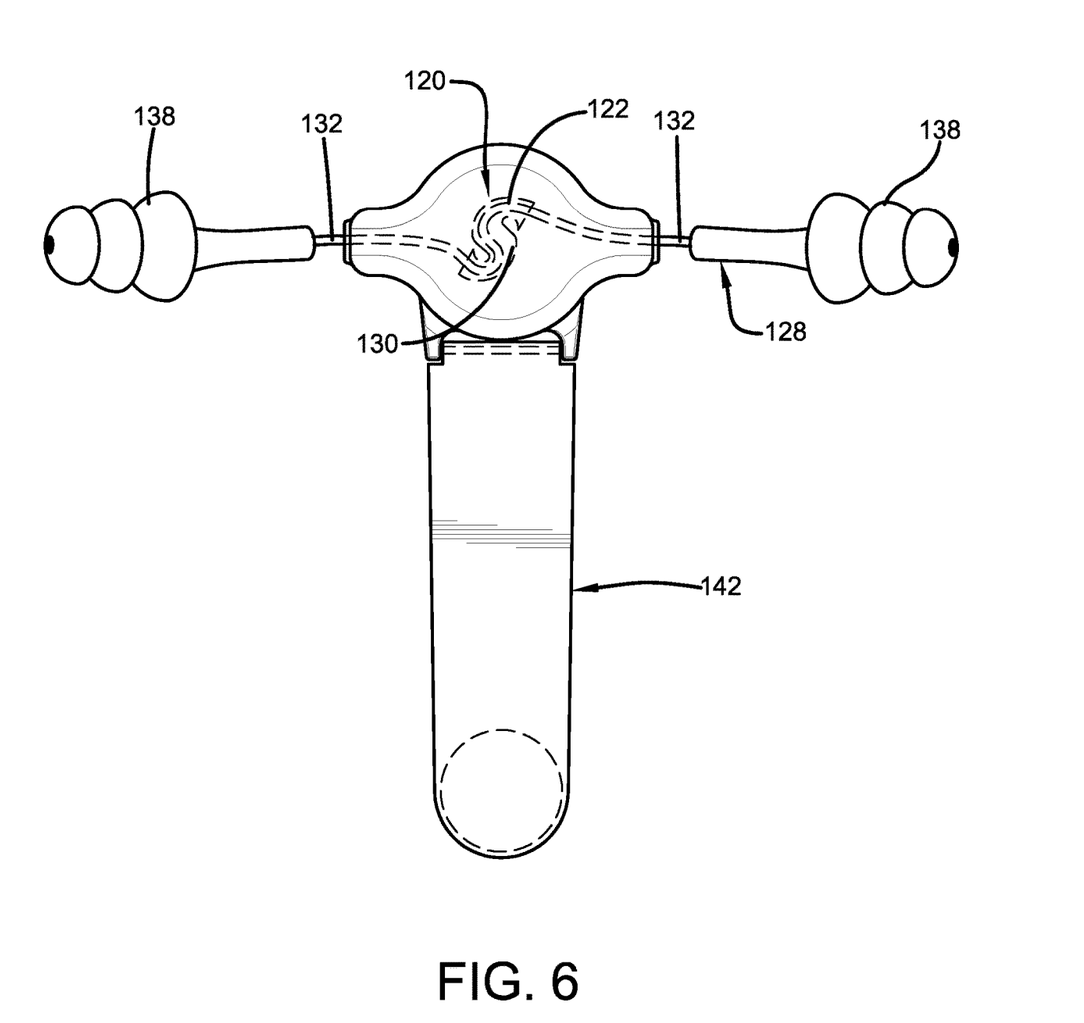
FIG. 6 illustrates a perspective view of the device in accordance with the disclosed architecture.
Figure 7:
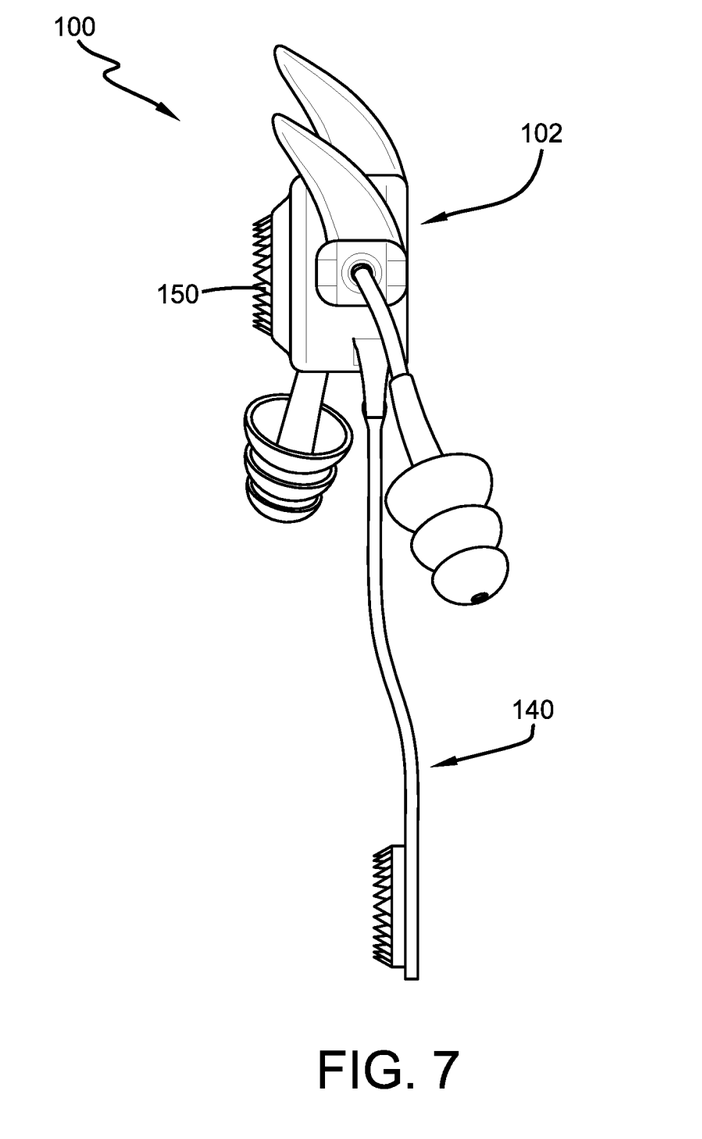
FIG. 7 illustrates a perspective view of a gripping element of the device in accordance with the disclosed architecture.

As illustrated in FIGS. 4, 4A, and 6, the recoil assembly 120 may comprise at least one reel 122 and at least one tension element 124 such as, but not limited to, a ratcheting component, a spring component, a tension bar, a braking mechanism, an automatic winder, or any other commonly used retraction mechanism. The recoil assembly 120 is encapsulated or enclosed within the housing 102 to protect the recoil assembly 120 from excessive wear or damage to the mechanism or other components.

The cord 128 is folded approximately in half and a midpoint 130 of the cord 128 is attached to the reel 122. The cord 128 is then wound around the reel 122 leaving a pair of cord ends 132 extended out of the housing 102. The cord 128 retractably engages the recoil assembly 120 or the tension element 124, so that as each of the pair of cord ends 132 is pulled away from the housing 102, the recoil assembly 120 tensions the cord 128 through the unwinding. Once fully extended out of the housing 102, the tension element 124, such as a ratchet, cam, clutch, or brake engages permitting the cord 128 to remain extended. The tension element 124 can engage the cord 128 at any point until it is fully extended to remove excessive slack from the system or to accommodate a user's preferences. To retract the cord 128, the user simply releases the tension element 124 by pulling the cord 128 slightly and allowing it to retract and rewind into the housing 102. The recoil assembly 120 may further comprise a duel ratchet system (not shown) so that the user may extend or retract each earbud simultaneously or independently.

The cord 128 is commonly constructed of plastic or organic materials but may comprise a wire or an encapsulated wire (not shown) for conducting a transmission, such an audio signal, a digital signal, a wireless signal, or the like. In this way, the device 100 may be used as earphones, earbuds, headphones, hearing aids, and the like in addition to hearing protection. For example, in one embodiment the device 100 could be used to communicate signals from a cellular device or other transmitter while still protecting the user from ambient sounds or other noise pollution. The transmission could be conducted through a contact connection or via a wireless signal such as a Bluetooth signal.

The device 100 further comprises a pair of ear engaging components 138 attachable to the cord 128. The ear engaging components 138 may comprise ear plugs, ear buds, head phones, or the like. In one embodiment the ear plugs may be foam, silicon, or plastic ear plugs insertable within an ear canal. The ear engaging components 138 are attachable to the pair of ends 132 of the cord 128. They may be permanently secured by adhesive, shrink wrap, or by any other similar means. Alternatively, the ear engaging components 138 may be replaceable in the event of wear, contamination, or other damage. Each of the pair of ends 132 may comprise a connector element 134. The ear engaging components 138 may attach to the pair of ends 132 of the cord 128 via the connector element 134. The connector element 134 may be a male/female connection, screws, clips, push and pull mechanisms, a quick detach mechanism, hook and loop fasteners, or the like. This allows the user to select from a variety of interchangeable ear engaging component 138 options useable with the device 100, such as but not limited to, conventional ear plugs, noise canceling plugs, custom fit plugs, plugs designed to be specific to a function, head phones, and the like.

The device 100 further comprises a mounting component 140 comprising a strap 142 and a securing element 144. The mounting component 140 is attachable to the housing 102 for engaging the wearable article 10 as illustrated in FIG. 8. The strap 142 is constructed from any kind of strapping material and is affixed, adhered, or otherwise permanently secured to the housing 102. The securing element 144 comprises a first portion 146 and a second portion 148 each of which is attached to the strap component. The securing element 144 may comprise magnets, hook and loop fasteners, buttons, snaps, clips, and the like, or any other means known to one of skill in the art of detachably attaching two points. In one embodiment, the securing element 144 comprises a pair of magnets attached to the ends of the strap 142. As such, the first portion 146 and the second portion 148 are the pair of magnets respectively.

In another embodiment, the top 104 of the housing 102 may comprise a magnet retaining portion 106 as illustrated in FIGS. 5, 5A, 6, and 7. The magnet retaining portion 106 comprises a chamfer element 108 or bevel. The housing 102 may further comprise a strap holding element 118. Then one end of the strap 142 attaches to the strap holding element 118 and does not have one of securing elements 144 attached. The free end of the strap 142 would still retain a magnet however as described supra. The second portion 148, or magnet, is then housed within the magnet retaining portion 106 of the housing 102 and is held in place by the chamfer element 108. The magnet attached to the strap 142 may then engage the magnet retained by the magnet retaining portion 106 of the housing 102 to secure the device 100 to the wearable article 10. Additionally, the securing element 144 may further comprise a gripping element 150, such as teeth capable of gripping cloth like material. A brush guard (not shown) may also be attached to or otherwise integrated with the housing 102 to help deflect branches or brush from bumping the device 100 and loosening the magnetic connection.

To use the device 100, the user selects an appropriate wearable article 10. In one example, the device 100 is attachable a hard hat. The strap 142 engages an existing opening in the hard hat, such as a size adjusting strap. This way, the integrity of the hard hat is not compromised. The strap 142 penetrates the opening, and the first portion 146 of the securing element 144 engages the second portion 148. In this example, the pair of magnets are brought close enough in proximity to attract each other, thereby temporarily securing the mounting component 140 to the hard hat.

When hearing protection is needed or is desirable, the user pulls the pair of ear engaging components 138 away from the housing 102 to a desired length and allows the recoil assembly 120 to temporarily lock the pair of ear engaging components 138 at that length. Each of the ear engaging components 138 is then inserted into the user's ears to provide hearing protection. Once there is no longer a need for protection, the ear engaging components 138 are removed from the user's ears. Then the user pulls on the ends 132 of the cord 128 to unlock the recoil assembly 120, and the cord 128 retracts back in to the housing 102 to secure the pair of ear engaging components 138 adjacent to the housing 102. The device 100 remains attached to the back of the hard hat out of the user's way until needed again. This permits the user to keep the device 100 conveniently close for reuse without the danger of misplacement.

Other variations are within the spirit of the present invention. Thus, while the invention is susceptible to various modifications and alternative constructions, a certain illustrated embodiment thereof is shown in the drawings and has been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A hearing protection device comprising:
   a housing comprising a top, a bottom, and a sidewall comprising a pair of openings;
   a recoil assembly comprising a tension element and a reel enclosed in an interior of the housing;
   a cord retractably engaging the tension element, the cord comprising a midpoint secured to the recoil assembly and a pair of ends that extend out of the housing;
   a pair of detachable ear engaging components attachable to the cord; and
   a mounting component attached to the housing for engaging a wearable article and
   wherein each of the pair of ends comprises a connector element for connecting each respective ear engaging component to each respective end of the cord.

2. The device of claim 1, wherein the cord is configured to transmit an audio signal.

3. The device of claim 1, wherein the cord is configured to transmit a digital signal.

4. The device of claim 1, wherein the mounting component comprises a strap and a securing element.

5. The device of claim 4, wherein the securing element is a pair of magnets attached to the strap.

6. A hearing protection device attachable to a wearable article, the hearing protection device comprising:
   a housing comprising a top, a bottom, and a sidewall comprising a pair of openings;
   a recoil assembly comprising a tension element and a reel enclosed in an interior of the housing;
   a cord retractably engaging the tension element, the cord comprising a midpoint secured to the recoil assembly and a pair of ends that extend out of the housing;
   a pair of detachable ear engaging components attachable to the cord; and
   a mounting component comprising a strap attached to the housing and a securing element; and
   wherein each of the pair of ends comprises a connector element for connecting each respective ear engaging component to each respective end of the cord; and
   wherein the top of the housing comprises a magnet retaining portion comprising a chamfer element configured to retain a magnet.

7. The device of claim 6, wherein the housing further comprises a strap holding element for holding one end of the strap.

8. The device of claim 6, wherein the securing element comprises a pair of magnets.

9. The device of claim 6, wherein the securing element comprises a toothed gripping element for engaging the wearable article.

10. The device of claim 6, wherein the cord is configured to transmit a wireless signal.

* * * * *